(12) United States Patent
Glidewell

(10) Patent No.: US 6,869,552 B2
(45) Date of Patent: Mar. 22, 2005

(54) BACK CASTING PREFABRICATED INCISAL VENEERS

(76) Inventor: James R. Glidewell, 201 Morningstar, Newport Beach, CA (US) 92660

( * ) Notice: Subject to any disclaimer, the term of this patent is extended or adjusted under 35 U.S.C. 154(b) by 0 days.

(21) Appl. No.: 10/105,601

(22) Filed: Mar. 25, 2002

(65) Prior Publication Data

US 2002/0175430 A1 Nov. 28, 2002

Related U.S. Application Data

(60) Provisional application No. 60/278,728, filed on Mar. 26, 2001.

(51) Int. Cl.$^7$ .......................... A61C 13/00; A61C 13/08
(52) U.S. Cl. .............................. 264/16; 264/19; 264/20
(58) Field of Search .............................. 264/16, 19, 20

(56) References Cited

U.S. PATENT DOCUMENTS

| | | | |
|---|---|---|---|
| 4,585,417 A | * | 4/1986 | Sozio et al. |
| 5,346,397 A | * | 9/1994 | Braiman |
| 5,827,063 A | | 10/1998 | Greenstein |
| 6,183,256 B1 | | 2/2001 | Fisher |
| 6,250,926 B1 | | 6/2001 | Foser |

* cited by examiner

Primary Examiner—Christopher A. Fiorilla
(74) Attorney, Agent, or Firm—Randall L. Reed; Levin & O'Connor

(57) ABSTRACT

An improved lost wax method for fabricating dental devices, a prefabricated incisal veneer (1) is selected from among a group of said veneers having predetermined shapes, shades, and sizes. Wax is applied (2 and 3) to the incisal veneer to create a wax buildup onto a model (4) or prefabricated coping (5). Subsequently, a sprue is attached to the applied wax (2 and 3) and the wax buildup is removed from the model (4) for investing and burnout to create a lost wax mold. For a crown with a substructure, the incisal veneer (1) and the coping (5) are both cast in place with press ceramic, press thermoplastic material, or by injecting a curable resin, composite, or epoxy material into the lost wax mold.

23 Claims, 2 Drawing Sheets

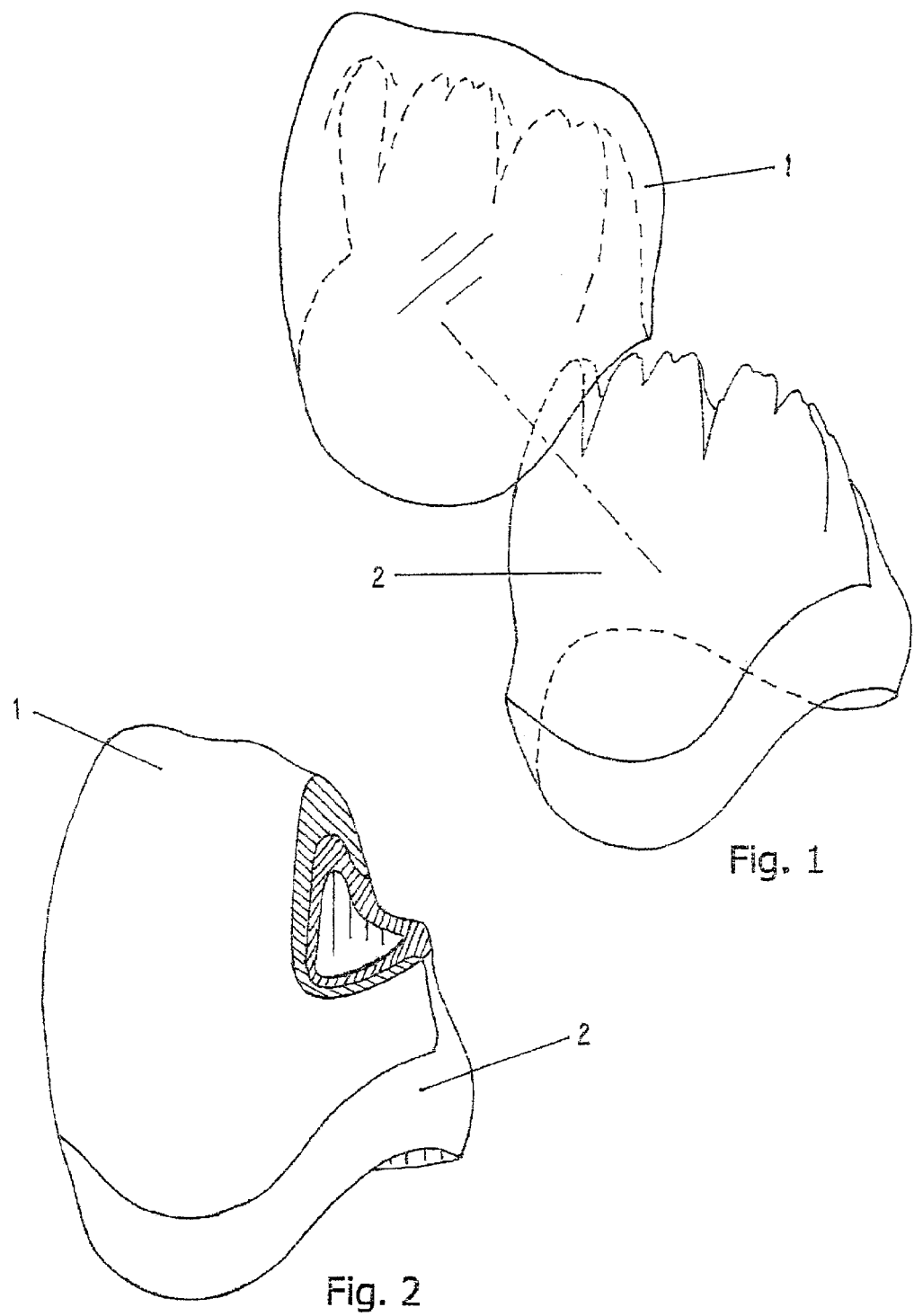

BACK CASTING PREFABRICATED INCISAL VENEERS

This application is entitled to the benefit of Provisional Patent Application Ser. No. 60/278,728, filed Mar. 26. 2001.

BACKGROUND—FIELD OF INVENTION

This invention relates to back casting of prefabricated incisal veneers to create polychromatic cast dental restorations.

BACKGROUND—DESCRIPTION OF PRIOR ART

The so-called "Lost-wax" method of preparing castings and molds therefrom, is well known to the art. Particularly, use of the lost-wax method within the dental profession for the purpose of casting partial frames; denture bases, crowns, bridges, veneers and other dental devices. The prior art of metal substrate and metal ceramic technology, for instance, has been a standard in clinical dentistry for more than thirty years and more recently, molten ceramic, molten plastic or other molten material may be pressed into a lost-wax mold.

The steps that are required to create variously pressed dental devices are similar in many respects as follows:

(a) An impression (negative mold) is taken—using hydrocolloid or other elastomeric dental impression material that may be removed without permanent deformation to the impression from undercut areas such as prepared or tilted teeth—to accurately reproduce a patient's oral situation.

(b) The impression is then used by the laboratory technician to create a stone or epoxy model which is a positive replica of the patient's oral situation. For instance, a model with removable dies may be used for making crown and bridge devices.

(c) Dies may be painted with a die spacer to allow for the thickness of dental cement or bonding agents that are used to secure the final restoration to the prepared teeth of patients.

(d) A lubricant or release agent may be placed over the model or die spacer material.

(e) A wax pattern is then fabricated over the model or a lubricated model or die.

(f) The model, including the wax pattern is then invested in high heat investment material, or the wax pattern is removed from the lubricated model or die and invested.

(g) The wax pattern is burned out of the investment material under high heat to form the lost-wax mold. A pressure molding system is used to press ceramic or other molten material into a lost-wax mold to make crown and bridge and other dental devices.

When making pressed ceramic devices, the shade of such devices will be determined and therefore limited by the shade of the ceramic ingot that is pressed in molten form into the lost wax mold. The use of the press-ceramic technique, as heretofore known, suffers from the disadvantage that the resulting pressed a dental device is monochromatic in appearance and thus lacks the blending of two or more colors, such as darker toward the gingival area, for a more natural-looking device. Moreover, a monochromatic look lacks the translucency that natural teeth exhibit, such as at the incisal edge where the enamel thins, and proximally where the enamel is not backed by dentin. While time consuming, pressed ceramic devices can be esthetically enhanced when cut back and layered over with porcelain to add color and translucency to incisal and proximal areas. However, the additional labor and processing time increase the cost to fabricate dental devices. Additionally, the anatomical detail and polychromatic appearance of such devices are dependant upon the skill of the dental technician and lack consistently dependable esthetic results. The present invention overcomes the practical limitations imposed by current press ceramic techniques by eliminating the need and additional cost of cutting back and layering to achieve more natural-looking color blending, and incisal and proximal translucency, by pressing ceramic to preformed shells within the lost-wax mold. Additionally, more predictably pleasing esthetics and greater uniformity of results, can be achieved with less dependency on the skill of the dental technician.

SUMMARY

In accordance with the present invention a prefabricated incisal veneer or shell pattern made of ceramic material is luted onto the stone die with wax or other material to form the final shape or wax buildup of the dental device to be fabricated. The die with the wax buildup, or only the wax buildup, is invested. The wax is burned out to form a lost-wax mold, said mold containing the prefabricated ceramic shell pattern within it. A molten press ceramic material is pressed into the lost-wax mold and against the prefabricated ceramic shell patten that lies within said mold. The resulting pressed ceramic dental devices with the prefabricated ceramic shell patterns cast in place may then be divested, polished, and adjusted as necessary.

Objects and Advantages

Accordingly, besides the objects and advantages of making press ceramic dental devices using a prefabricated ceramic shell patterns in my above patent, several objects and advantages of the present invention are:

(a) To provide a crown and bridge fabrication technique that is as easy as forming wax or other malleable material and utilizes preformed ceramic incisal veneers.

(b) To enable dental technicians to more consistently fabricate dental devices that exhibit proper anatomical details and polychromatic appearances resembling those of the natural teeth.

(c) To provide more esthetic dental devices than heretofore possible in a single pressing of ceramic, having translucency and color that are close to those of the natural teeth, (d) To provide a pressed ceramic technique that is less costly, by eliminating the necessity of additional skilled labor and processing time required to cut back pressed devices and to layer on additional porcelain materials to achieve more natural-looking color blending and translucency.

(e) To provide a technique for making more esthetic dental devices that is a faster and easier method to teach than heretofore possible.

(f) To provide a technique for achieving a predictable and a uniform final restorative result, as may ordinarily be achieved only by the most highly skilled technicians.

Further objects and advantages of using prefabricated incisal veneers and press ceramic is that it enables an inexperienced dental technician to consistently fabricate dental devices that exhibit more uniform esthetics and appearances. Still further objects and advantages will become apparent from a consideration of the ensuing description and drawings.

DRAWING FIGURES

In the drawings, closely related figures have the same number but different alphabetic suffixes.

FIG. 1 shows a prefabricated crown form, in exploded view of a crown form, consisting of a prefabricated ceramic incisal veneer, and pre-applied wax.

FIG. 2 shows a cutaway drawing of a prefabricated crown form, consisting of a prefabricated ceramic incisal veneer in the form of a facial/incisal shell pattern. Additionally, a pre-applied wax material completes the desired anatomical details of the crown form.

Figure 3A:
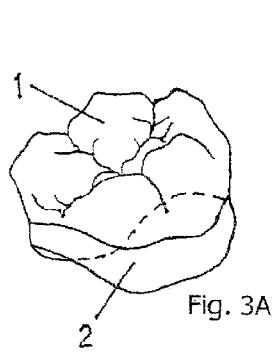
Figure 3B:
Figure 3C:
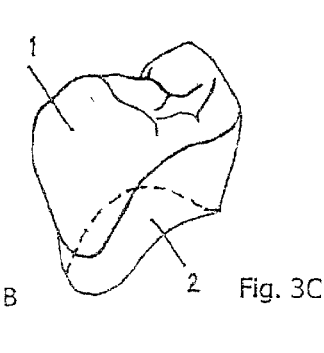

FIGS. 3A through 3C show three embodiments of prefabricated crown forms. FIG. 3A shows a posterior molar crown form consisting of a prefabricated incisal veneer in the form of a buccal/occlusal shell pattern, and pre-applied wax. FIG. 3B shows a lower anterior crown form consisting of a facial/incisal shell pattern, with pre-applied wax. FIG. C shows a posterior bicuspid or premolar crown form consisting of an incisal veneer in the form of a buccal/occlusal shell pattern, and pre-applied wax.

Figure 4:
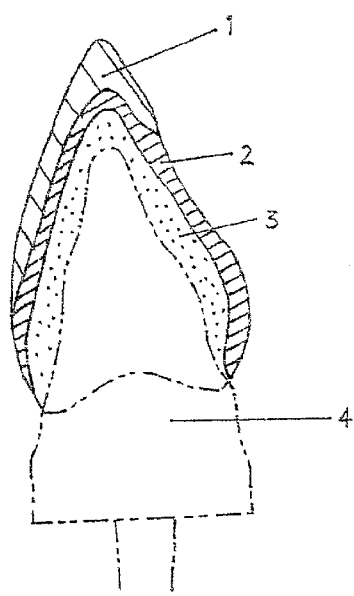

FIG. 4 shows a completed wax buildup using a prefabricated crown form. The crown form consists of an incisal veneer in the form of facial/incisal shell, and pre-applied wax. A soft wax material is applied as needed to position a prefabricated crown form onto a model. A wax sprue (not shown) is attached to the wax buildup on the lingual side of the completed wax-up.

Figure 5:
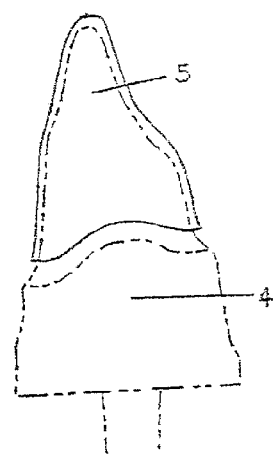
Figure 6:
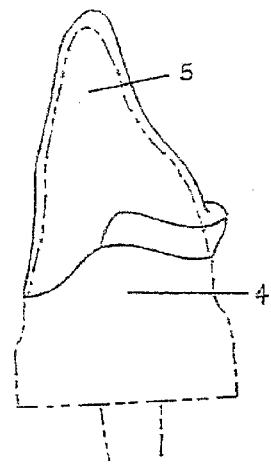

FIGS. 5 and 6, show embodiments of dental copings that may be used, in conjunction with the method disclosed in FIGS. 1 through 4. FIG. 5 shows a coping for a single unit dental device "crown" with all-porcelain margins, and FIG. 6 shows a coping for a crown with a labial collar. Other coping designs (not shown) for crowns may be used, and an understructure (not shown) for a multi unit dental device "bridge" also may be used. Metal, ceramic or other material for making crown copings and bridge understructures may be used to serve as substrate materials.

REFERENCE NUMERALS IN DRAWINGS

1 Incisal veneer
2 Pre-applied wax
3 Applied wax
4 Model
5 Coping

Objects and Advantages

DESCRIPTION—FIGS. 1 through 4—Preferred Embodiments

A preferred embodiment of the present invention is illustrated in FIG. 1 (exploded view), FIG. 2 (cutaway view), FIGS. 3A through 3C (embodiments of crown forms), and FIG. 4 (completed wax buildup). In FIGS. 1 through 2 and FIGS. 3A through 3B, various crown forms are illustrated using prefabricated incisal veneers 1 in facial/incisal and buccal/occlusal shell patterns, and pre-applied wax 2 which is applied up to the gingival contour and including some or all of the desired lingual anatomy as an aid to quick and more uniform fabrication of wax buildups. The prefabricated ceramic incisal veneer can be made of pressed or powdered ceramic that is formed and fired. Soft wax is applied 3 to position the crown form onto a model 4 and complete the wax buildup (FIG. 4). A sprue is attached to the wax buildup (not shown), and the wax buildup is removed from the model 4 for investing and burnout to create a lost-wax mold, wherein the incisal veneer 1 is cast in place using press ceramic.

FIGS. 5 and 6—Additional Embodiments

In an additional embodiment of my invention, soft wax is applied 3 to position the crown form onto a coping 5 so that the coping 5 provides a substructure for the completed wax buildup. FIGS. 5 and 6 illustrate coping designs, although other designs such as a mesh design as claimed in my invention may be used. Additionally, any dental substrate material may be used to fabricate a coping 5 or bridge understructure (not shown), such as metal, zirconia, or bulk metallic glass materials as claimed in my invention. When the wax buildup is complete, a sprue (not shown) is attached to the wax buildup, and the wax buildup is removed from the model 4 for investing and burnout to create a lost wax mold, wherein the incisal veneer 1 and the coping 5 are cast in place using press ceramic.

FIGS. 1 through 6—Alternative Embodiments

The incisal veneer 1 may be positioned directly onto the model 4 or coping 5 by applying wax 3. Pigments and colored ceramic materials may be applied and fired onto the incisal veneer 1 before applying wax 3. Additionally, there are various dental materials that can be pressed into a lost wax mold. Rather than using press ceramic, after the lost wax mold containing the incisal veneer 1 is created, the incisal veneer 1 may be cast in place using a press thermoplastic material, or by injecting a curable resin, composite, or epoxy material. Similarly, if a coping 5 is required, the incisal veneer 1 and the coping 5 may be cast in place using a press thermoplastic material, or by injecting a curable resin or composite material into the lost wax mold.

ADVANTAGES

From the description above, a number of advantages of my a back cast method using prefabricated incisal veneers of become evident:

(a) My invention of back casting prefabricated incisal veneers overcomes present limitations inherent in applying the lost wax, press ceramic method for making dental devices by enabling the fabrication of esthetic dental devices in a single pressing.

(b) Dental devices can be fabricated with more predictable and acceptable esthetics results.

(c) Dental devices can be fabricated in less time and with less skilled labor and are therefore less costly to make.

OPERATION

In accordance with one aspect of the present invention, there is provided a process for the preparation of a dental crown restoration, which comprises preparing a plurality of prefabricated incisal veneers in predetermined lengths, widths, shapes, colors, and combinations of hue, value and chroma resembling those of the natural teeth.

The manner of back casting prefabricated incisal veneers to fabricate dental devices is similar to that for using the traditional method of making pressed ceramics. Namely, wax is used to complete the final shape or wax buildup of the dental device to be fabricated. Wax may be applied onto a die or onto a cast metal coping or other coping material which serves as a substrate material. A special "margin wax" may be used to more definitively define marginal details. Additionally, polymerizable waxes of light-curing or self-curing resin compositions that polymerize without shrinking, and are stronger and more elastic than wax when cured, and that can be molded and are more easily manipulated compared to molten wax, may be used as a wax buildup material, or as pre-applied wax to the prefabricated incisal veneers. A wax sprue is attached to a portion of the wax buildup. After investing and burnout, the resulting lost wax pattern is used to fabricate a dental device using press ceramic material, and the resultant cast dental device is adjusted, polished and glazed in the usual manner.

CONCLUSION, RAMIFICATIONS, AND SCOPE

Accordingly, the reader will see that the method of this invention of back casting prefabricated incisal veneers to make pressed ceramic dental devices is more productive than using cut back and build up techniques and will increase the usefulness of the lost-wax, press-ceramic method to make dental devices. Using my method of back casting prefabricated incisal veneers, inexperienced dental technicians can be more easily taught to achieve predictably esthetic results and finished dental devices can be fabricated more quickly and at less cost that than other fabrication methods such as individually firing of hand-stacked porcelain devices.

The prefabricated ceramic incisal veneers also may be pre-waxed in part, such as up to the gingival contour to include some or all of the desired lingual anatomy, as an aid to quick fabrication and to provide more consistently functional results. A plurality of prefabricated incisal veneers in predetermined widths, contours, colors and predetermined combinations of hues, values and chroma may be selected according size requirements and the shade and age of the patient. Metal or other substrate materials may be used to provide added strength to the final restoration.

Although the description above contains many specifics, these should not be construed as limiting the scope of the invention but as merely providing illustrations of some of the presently preferred embodiments of this invention. Thus the scope of the invention should be determined by the appended claims and their legal equivalents, rather than by the examples given.

What I claim as my invention is:

1. A method for making a press ceramic dental restorative device in the nature of a crown or a bridge, comprising the steps of:
    a) providing a prefabricated ceramic incisal veneer of press ceramic or powdered ceramic that is formed and fired;
    b) applying wax to said incisal veneer to fabricate a wax buildup;
    c) attaching a sprue to said wax buildup; and,
    d) back casting said incisal veneer in a lost wax mold with press ceramic to fabricate said device with said incisal veneer cast in place by:
        1) investing the applied wax;
        2) burning out the wax to create a lost wax mold; and
        3) pressing molten ceramic into the lost wax mold against the veneer.

2. A method according to claim 1 wherein said step of providing a prefabricated incisal veneer further includes a step of selecting said incisal veneer from among a group of prefabricated incisal veneers having predetermined shapes, shades, and sizes.

3. A method according to claim 2 wherein wax is pre-applied to said group of prefabricated incisal veneers having predetermined shapes and sizes.

4. A method according to claim 1, further including the step of:
    providing a prefabricated understructure before step d) and casting in place said understructure together with said incisal veneer.

5. A method according to claim 4 wherein said understructure is a ceramic material.

6. A method according to claim 4 wherein said understructure is a bulk metallic glass material.

7. A method according to claim 4 wherein said understructure is a mesh design.

8. A method according to claim 1 wherein said wax is a polymerizable wax.

9. A method according to claim 1 wherein said step of providing a prefabricated incisal veneer further includes a step of selecting, applying and firing pigment or colored ceramic paste to the underside of said incisal veneer before step b).

10. A method for making a dental restorative device in the nature of a crown or a bridge, comprising the steps of:
    a) providing a prefabricated ceramic incisal veneer of press ceramic or powdered ceramic that is formed and fired;
    b) applying wax to said incisal veneer to fabricate a wax buildup;
    c) attaching a sprue to said wax buildup; and,
    d) back casting said incisal veneer in a lost wax mold with press thermoplastic material to fabricate said device with said incisal veneer cast in place by:
        1) investing the applied wax;
        2) burning out the wax to create a lost wax mold; and
        3) pressing molten ceramic into the lost wax mold against the veneer.

11. A method according to claim 10 wherein said step of providing a prefabricated incisal veneer further includes a step of selecting said incisal veneer from among a group of prefabricated incisal veneers having predetermined shapes, shades, and sizes.

12. A method according to claim 11 wherein wax is pre-applied to said group of prefabricated incisal veneers having predetermined shapes and sizes.

13. A method according to claim 10, further including the step of:
    providing a prefabricated metal understructure before step d) and casting in place said understructure together with said incisal veneer.

14. A method according to claim 13 wherein said understructure is zirconia.

15. A method according to claim 13 wherein said understructure is a bulk metallic glass material.

16. A method according to claim 13 wherein said understructure is a mesh design.

17. A method according to claim 10 wherein said wax is a polymerizable wax.

18. A method according to claim 10 wherein said step of providing a prefabricated incisal veneer further includes a step of selecting, applying and firing pigment or colored ceramic paste to the underside of said incisal veneer before step b).

19. A method for making a dental restorative device in the nature of a crown or a bridge, comprising the steps of:
    a) providing a prefabricated ceramic incisal veneer of press ceramic or powdered ceramic that is formed and fired;
    b) applying wax to said incisal veneer to fabricate a wax buildup;
    c) attaching a sprue to said wax buildup; and,
    d) back casting said incisal veneer in a lost wax mold by injecting a curable resin, composite or epoxy material into said mold to fabricate said device with said incisal veneer cast in place by:
        1) investing the applied wax;
        2) burning out the wax to create a lost wax mold; and
        3) injecting a curable resin, composite or epoxy material into said-lost was mold against the veneer.

20. A method according to claim 19, further including the step of:
    providing a prefabricated metal understructure before step d) and casting in place said understructure together with said incisal veneer.

21. A method according to claim 5 wherein said ceramic material is zirconia.

22. A method according to claim 4 wherein said understructure is a metal.

23. A method according to claim 13 wherein said understructure is a metal.

* * * * *